(12) United States Patent
Sheng et al.

(10) Patent No.: US 12,005,059 B2
(45) Date of Patent: Jun. 11, 2024

(54) NEMONOXACIN MALATE ACTIVE PHARMACEUTICAL INGREDIENT WITH LOW COMBINATION IMPURITIES, AND A PREPARATION METHOD THEREOF

(71) Applicant: ZHEJIANG MEDICINE CO., LTD. XINCHANG PHARMACEUTICAL FACTORY, Zhejiang (CN)

(72) Inventors: Li Sheng, Zhejiang (CN); Gang Fan, Zhejiang (CN); Dadong Shen, Zhejiang (CN); Guofeng Wu, Zhejiang (CN); Xufeng Wu, Zhejiang (CN); Haoling Gao, Zhejiang (CN); Lanfang Zhu, Zhejiang (CN)

(73) Assignee: ZHEJIANG MEDICINE CO., LTD. XINCHANG PHARMACEUTICAL FACTORY, Shaoxing (CN)

( * ) Notice: Subject to any disclaimer, the term of this patent is extended or adjusted under 35 U.S.C. 154(b) by 0 days.

(21) Appl. No.: 18/079,019

(22) Filed: Dec. 12, 2022

(65) Prior Publication Data

US 2023/0201189 A1 Jun. 29, 2023

(30) Foreign Application Priority Data

Oct. 26, 2021 (CN) .......................... 202111250494.5

(51) Int. Cl.
  *A61K 31/4709* (2006.01)
(52) U.S. Cl.
  CPC ............................ *A61K 31/4709* (2013.01)

(58) Field of Classification Search
  CPC .................................................. A61K 31/4709
  See application file for complete search history.

(56) References Cited

U.S. PATENT DOCUMENTS

| | | | |
|---|---|---|---|
| 8,039,485 B2 * | 10/2011 | Redman-Furey | C07D 401/04 546/156 |
| 8,211,909 B2 * | 7/2012 | Hsu | A61P 31/12 514/312 |
| 8,658,183 B2 * | 2/2014 | Lee | A61P 11/02 514/312 |
| 11,731,955 B2 * | 8/2023 | Dong | C07D 401/12 546/153 |

OTHER PUBLICATIONS

Dhawle, Chem Sci Rev Lett, 2018, 7(25), 368-372. (Year: 2018).*

* cited by examiner

*Primary Examiner* — D Margaret M Seaman
(74) *Attorney, Agent, or Firm* — Samson G. Yu

(57) ABSTRACT

Provided in the present disclosure are a nemonoxacin malate active pharmaceutical ingredient with low combination impurities, and a preparation method thereof, specifically, provided in the present disclosure is a method for preparing the nemonoxacin malate active pharmaceutical ingredient, the method includes the following steps: 1) providing a C1-C3 alcohol/water mixed solvent in which nemonoxacin free base (Formula II) and D,L-malic acid are dissolved; and 2) performing cooling crystallization on a mixed solution obtained in the step 1), and then performing solid-liquid separation, washing and drying on a precipitated solid, so as to obtain the nemonoxacin malate active pharmaceutical ingredient.

14 Claims, 14 Drawing Sheets

NEMONOXACIN MALATE ACTIVE PHARMACEUTICAL INGREDIENT WITH LOW COMBINATION IMPURITIES, AND A PREPARATION METHOD THEREOF

TECHNICAL FIELD

The present disclosure relates to the field of pharmaceutical analysis, specifically, provided in the present disclosure are a nemonoxacin malate active pharmaceutical ingredient with low combination impurities, and a preparation method thereof.

BACKGROUND

The chemical name of nemonoxacin malate is butanedioicacid, 2-hydroxy-,compd.with7-[(3S,5S)-3-amino-5-methyl-1-piperidinyl]-1-cyclopropyl-1,4-dihydro-8-methoxy-4-oxo-3-quinolinecarboxylic acid, the nemonoxacin malate is the first fluorine-free quinolone antimicrobial drug in the world developed by Procter & Gamble, phase II clinical studies of the nemonoxacin malate in community pneumonia and diabetic foot infections have been completed in the United States, and the effect is significant.

Active Pharmaceutical Ingredient (API) refers to raw material drug used for producing various preparations, and is an active ingredient in the preparation. The API is well defined in ICH Q7A as any one of substances or a mixture of substances used in pharmaceutical manufacturing, and becomes an active ingredient of a drug when being used in pharmaceutical manufacturing. The substance has a pharmacological activity or other direct effect in the diagnosis, treatment, relief of symptoms, management or prevention of diseases, or can affect the function or structure of the body.

Among current methods for preparing a nemonoxacin malate API as reported in open publications, for example, disclosed in embodiment 1 of CN 101045725 B is a method for preparing a D,L-malate hemihydrate of nemonoxacin, the method includes: successively adding nemonoxacin free base (Formula II) and D,L-malic acid into 95% ethanol, then performing heating to a reflux temperature (about 80° C.), and adding a small amount of water until the mixture is completely dissolved; decolorizing a reaction solution with activated carbon, and performing filtration; and cooling the filtrate to 45° C., holding the temperature for more than 2 h, then performing further cooling to 5° C., and performing suction filtration, washing and drying, so as to obtain the nemonoxacin malate API. According to the salifying method, the composition of the D,L-malic acid and the nemonoxacin free base (Formula II) in the obtained API has high impurities, resulting in low yield.

The impurities in the nemonoxacin malate or any API are not required. In extreme cases, the impurities may even be harmful to patients who are treated with API-containing dosage forms. In a process of the formation of D,L-malate from the nemonoxacin, corresponding composition impurities are easily produced. Therefore, there is an urgent needed to provide a nemonoxacin malate API with low combination impurities and a related preparation method in the present disclosure.

SUMMARY

The present disclosure is intended to provide a nemonoxacin malate Active Pharmaceutical Ingredient API) with low impurity content (Formula I):

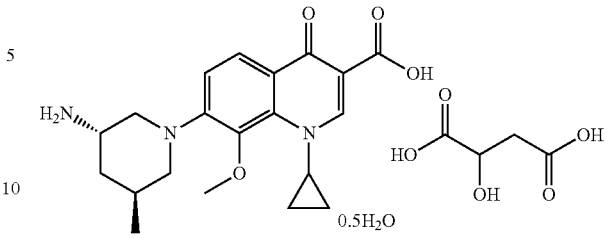

Formula 1

A first aspect of the present disclosure provides a method for preparing the nemonoxacin malate API, the method includes the following steps:
1) wherein, a C1-C3 alcohol/water mixed solvent in which nemonoxacin free base (Formula II) and D,L-malic acid are dissolved is provided, and the temperature of the mixed solvent is 50° C.-65° C.:
   a feeding mole ratio of the D,L-malic acid to the nemonoxacin free base is 0.95:1.0-1.2:1.0, the use amount of the C1-C3 alcohol/water mixed solvent is 8-14 times the weight of the nemonoxacin free base; and a weight ratio of the water to the C1-C3 alcohol is 0.4-0.7:1;
2) cooling crystallization is performed on a mixed solution obtained in the step 1), and then solid-liquid separation, washing and drying are performed on a precipitated solid, so as to obtain the nemonoxacin malate API.

In another preferred embodiment, the C1-C3 alcohol is ethanol.

In another preferred embodiment, the temperature of the mixed solvent is 55° C.-60° C.

In another preferred embodiment, the use amount of the C1-C3 alcohol/water mixed solvent is 10-12 times the weight of the nemonoxacin free base.

In another preferred embodiment, the weight ratio of water to C1-C3 alcohol is 0.5-0.6:1.

In another preferred embodiment, the feeding mole ratio of the D,L-malic acid to the nemonoxacin free base is 0.98:1.03-1.05:1.0.

In another preferred embodiment, the feeding mole ratio of the D,L-malic acid to the nemonoxacin free base is 1.00:1.02-1.0.

In another preferred embodiment, in the C1-C3 alcohol/water mixed solution, the use amount of the mixed solvent is 10-12 times the weight of the nemonoxacin free base.

In another preferred embodiment, a weight ratio of the water to the C1-C3 alcohol is 0.5-0.6:1.

In another preferred embodiment, before cooling crystallization, the method further includes the following step: using activated carbon to decolorize the mixed solution.

In another preferred embodiment, the method includes the following step: decolorizing the obtained mixed solution with activated carbon at 50° C.-65° C., and obtaining filtrate after hot filtration.

In another preferred embodiment, the method includes the following step: performing the decolorization by using the activated carbon of which weight is 1%-20% of the weight of the nemonoxacin free base.

In another preferred embodiment, the time for the decolorization is 1-60 min, preferably 10-30 min.

In another preferred embodiment, the mixed solution is filtered and decolorized on line by means of an activated carbon filter.

In another preferred embodiment, the cooling crystallization refers to direct cooling crystallization, and the direct cooling crystallization includes: cooling the mixed solution to room temperature, and then performing cooling to −10° C.-20° C., preferably −10° C.-10° C., and more preferably −5° C.-5° C. by means of an ice bath for crystallization.

In another preferred embodiment, the cooling crystallization refers to gradient, the gradient cooling crystallization includes the following steps:

(i) the mixed solution is cooled to 35° C.-45° C., then the temperature is held and stirring is performed for 0.5-6 h, preferably 1-4.5 h, and more preferably 1-3 h.

(ii) filtrate obtained in the step (i) is cooled to −10° C.-20° C., preferably −10° C.-10° C., and more preferably −5° C.-5° C. for crystallization.

(iii) the filtrate after the crystallization is filed, a filter cake is washed with ethanol, and then vacuum drying is performed on the filter cake at 20° C.-65° C., preferably 30-60° C., and more preferably 40-50° C. so as to obtain the nemonoxacin malate API.

A second aspect of the present disclosure provides a nemonoxacin malate API with low combination impurities prepared by means of the method as described in the first aspect of the present disclosure:

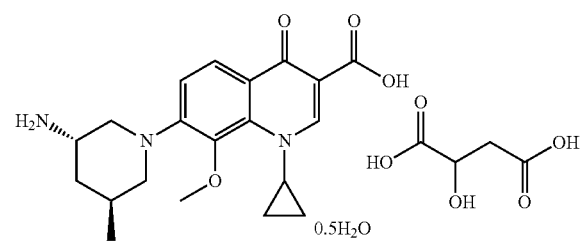

the API contains one or more of impurities selected from the following group: an impurity A, an impurity B, an impurity C, and an impurity D:

the impurity A:

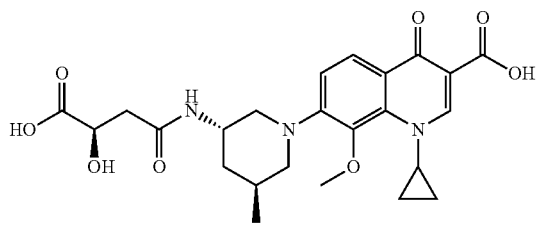 [SMILES: COc1c(N2C[C@@H](C)C[C@H](NC(=O)C[C@@H](O)C(=O)O)C2)ccc2c(=O)c(C(=O)O)cn(C3CC3)c12]

the impurity B:

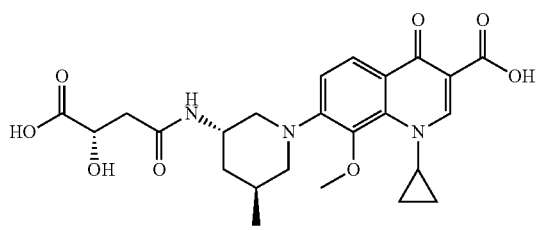 [SMILES: COc1c(N2C[C@@H](C)C[C@H](NC(=O)C[C@H](O)C(=O)O)C2)ccc2c(=O)c(C(=O)O)cn(C3CC3)c12]

the impurity C:

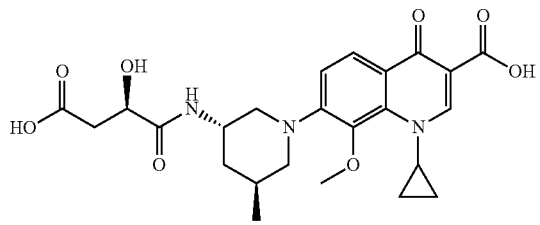 [SMILES: COc1c(N2C[C@@H](C)C[C@H](NC(=O)[C@H](O)CC(=O)O)C2)ccc2c(=O)c(C(=O)O)cn(C3CC3)c12]

the impurity D:

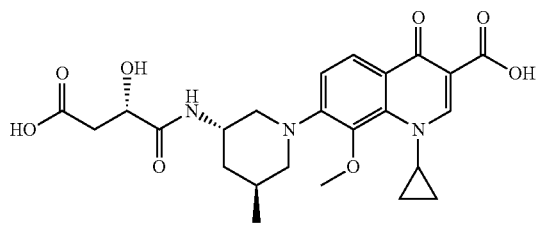 [SMILES: COc1c(N2C[C@@H](C)C[C@H](NC(=O)[C@@H](O)CC(=O)O)C2)ccc2c(=O)c(C(=O)O)cn(C3CC3)c12]

In another preferred embodiment, in the API, the sum of the impurity A, the impurity B, the impurity C, and the impurity D is not greater than 0.15 wt %.

It should be understood that, within the scope of the present disclosure, each of the above technical features of the present disclosure and each of the technical features specifically described below (for example, embodiments) can be combined with each other, so as to constitute new or preferred technical solutions, due to the limitation of space, details are not described herein again.

DETAILED DESCRIPTION OF THE EMBODIMENTS

Figure 1:
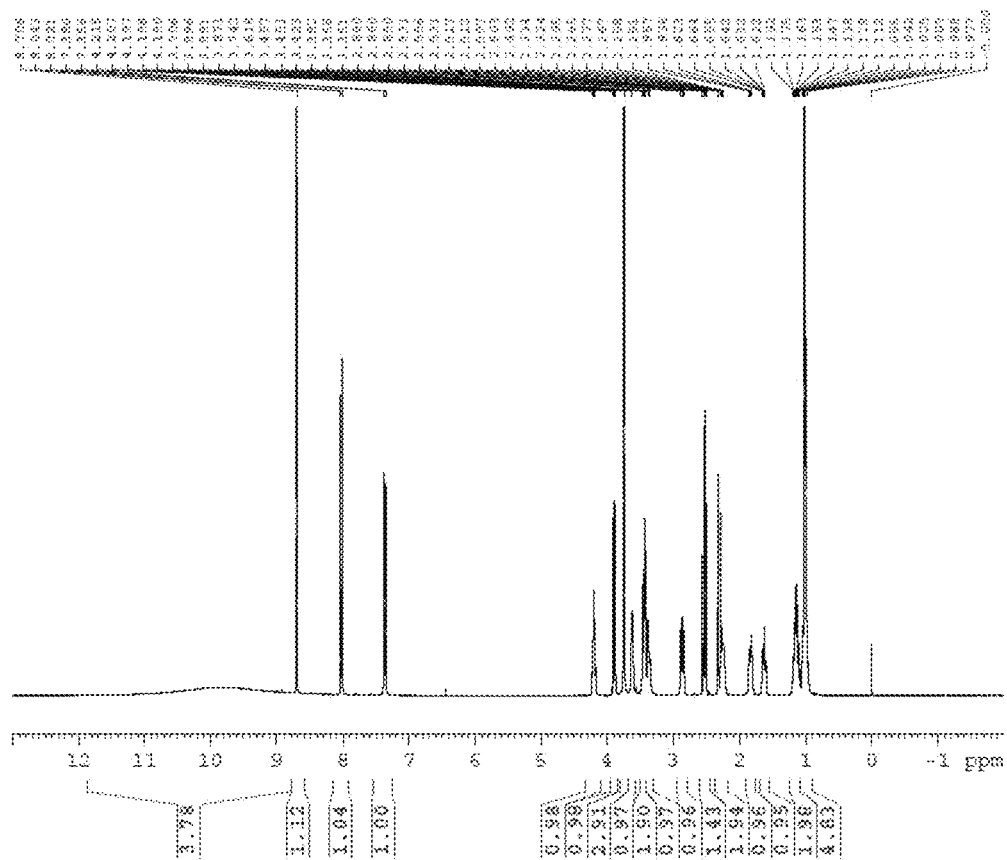
FIG. 1 is a nuclear magnetic resonance hydrogen spectrum of the nemonoxacin malate.
Figure 2:
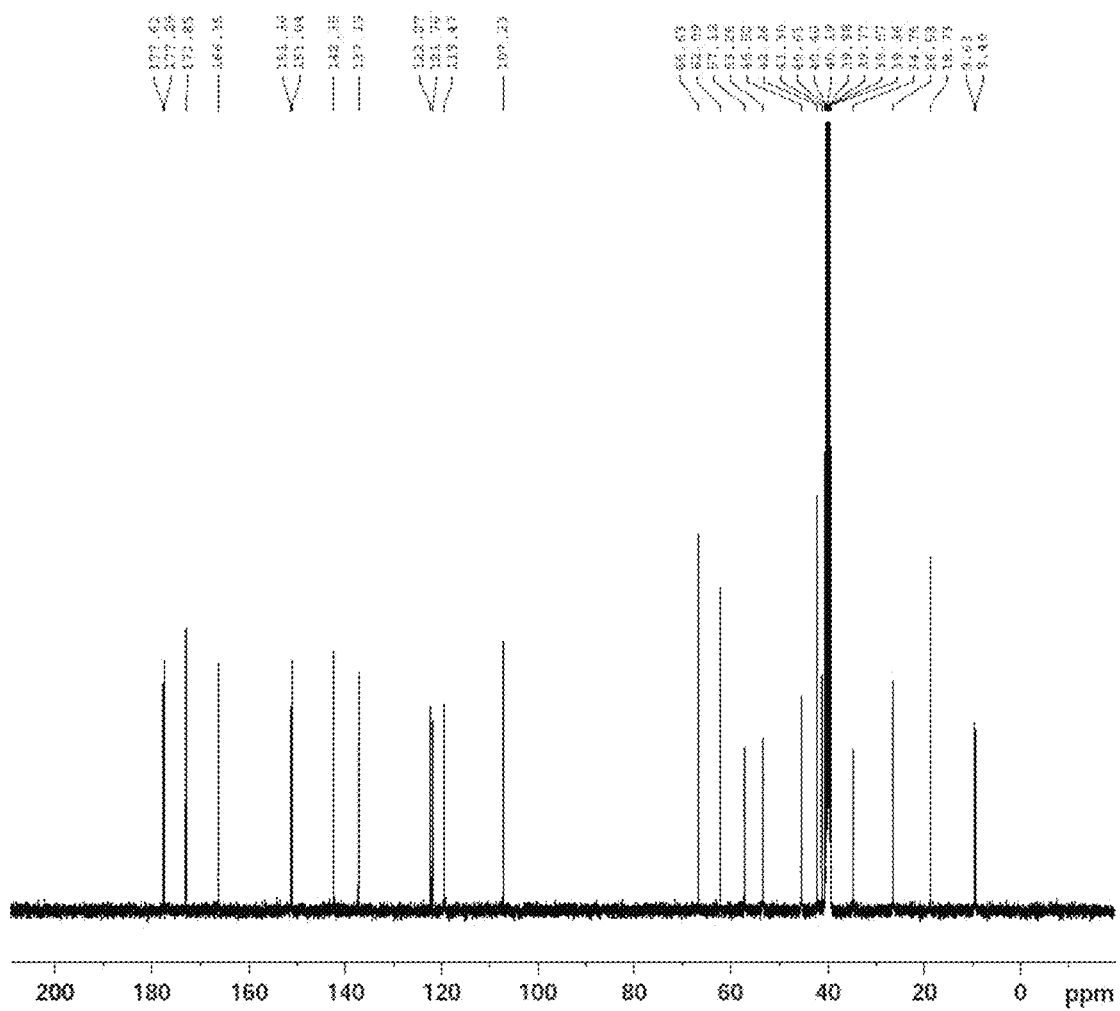
FIG. 2 is a nuclear magnetic resonance carbon spectrum of the nemonoxacin malate.
Figure 3:
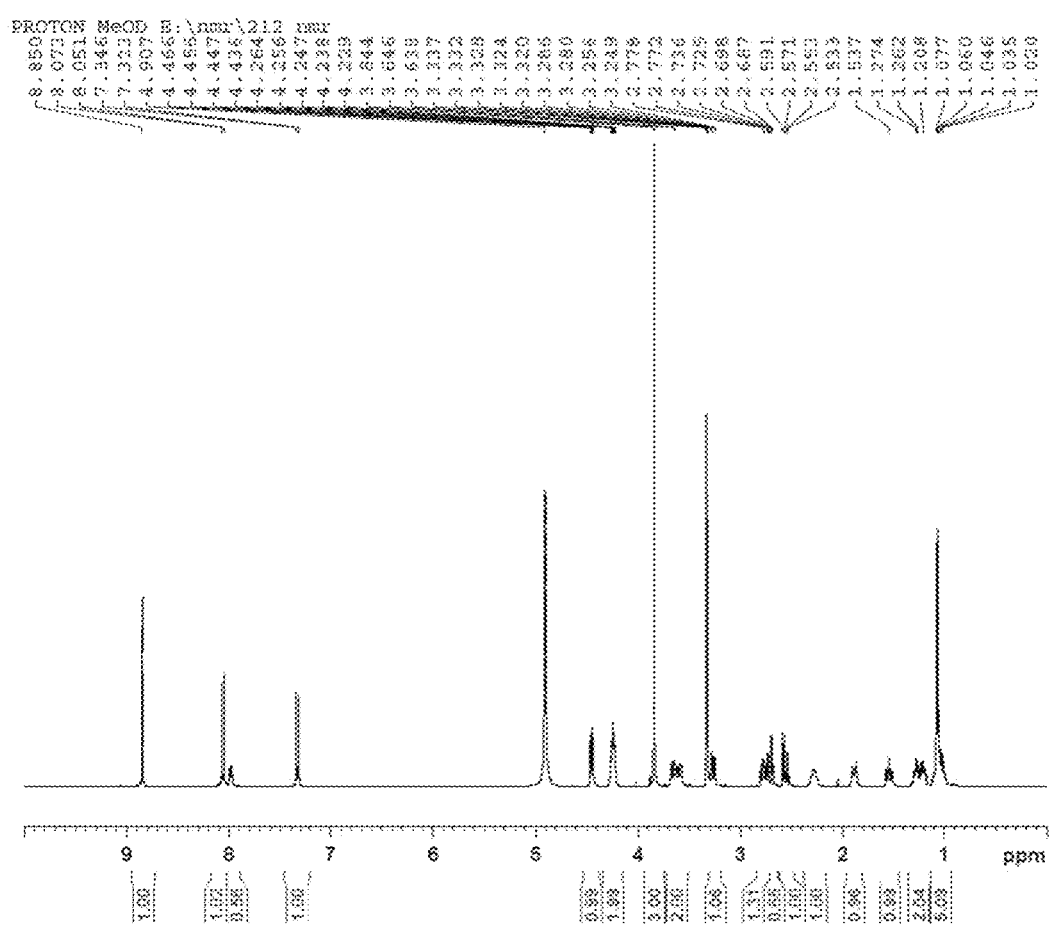
FIG. 3 is a nuclear magnetic resonance hydrogen spectrum of the impurity A.
Figure 4:
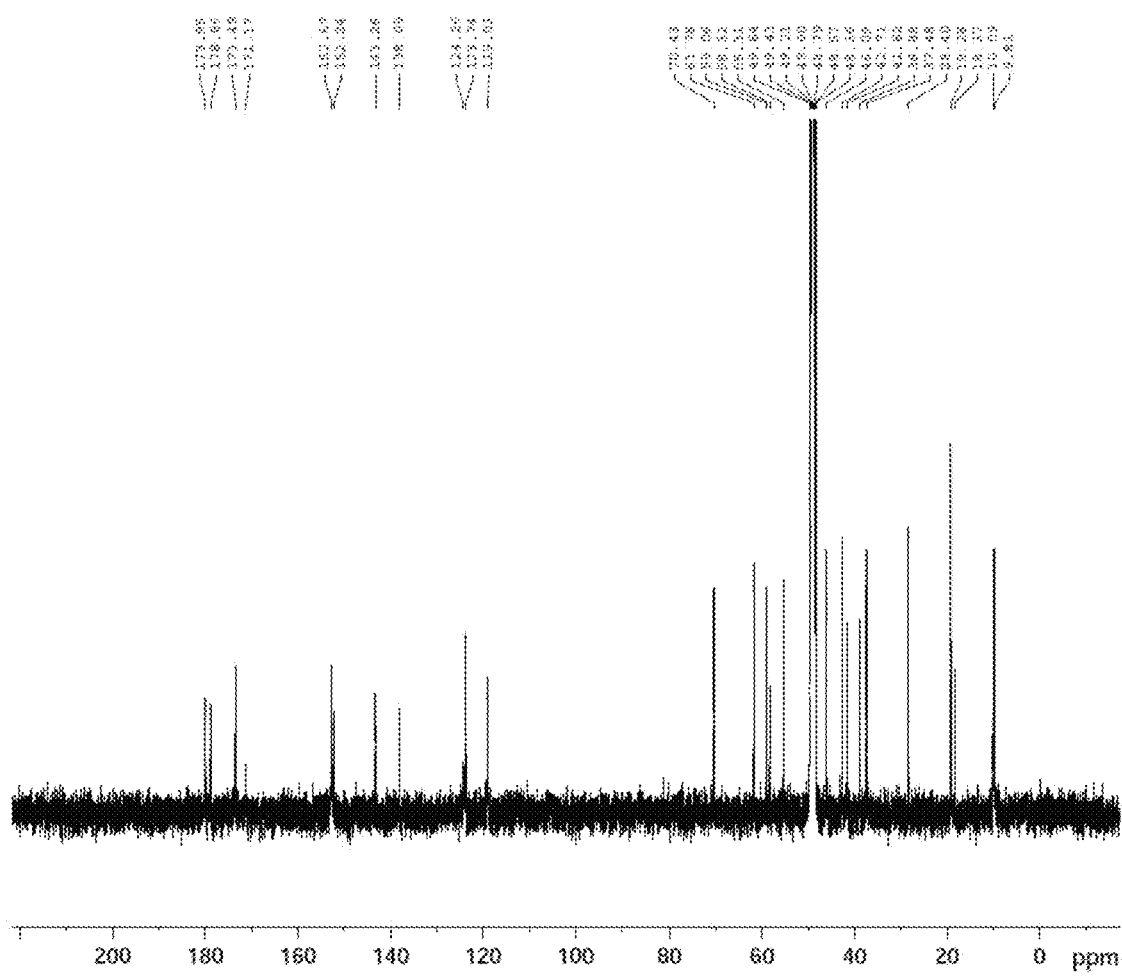
FIG. 4 is a nuclear magnetic resonance carbon spectrum of the impurity A.
Figure 5:
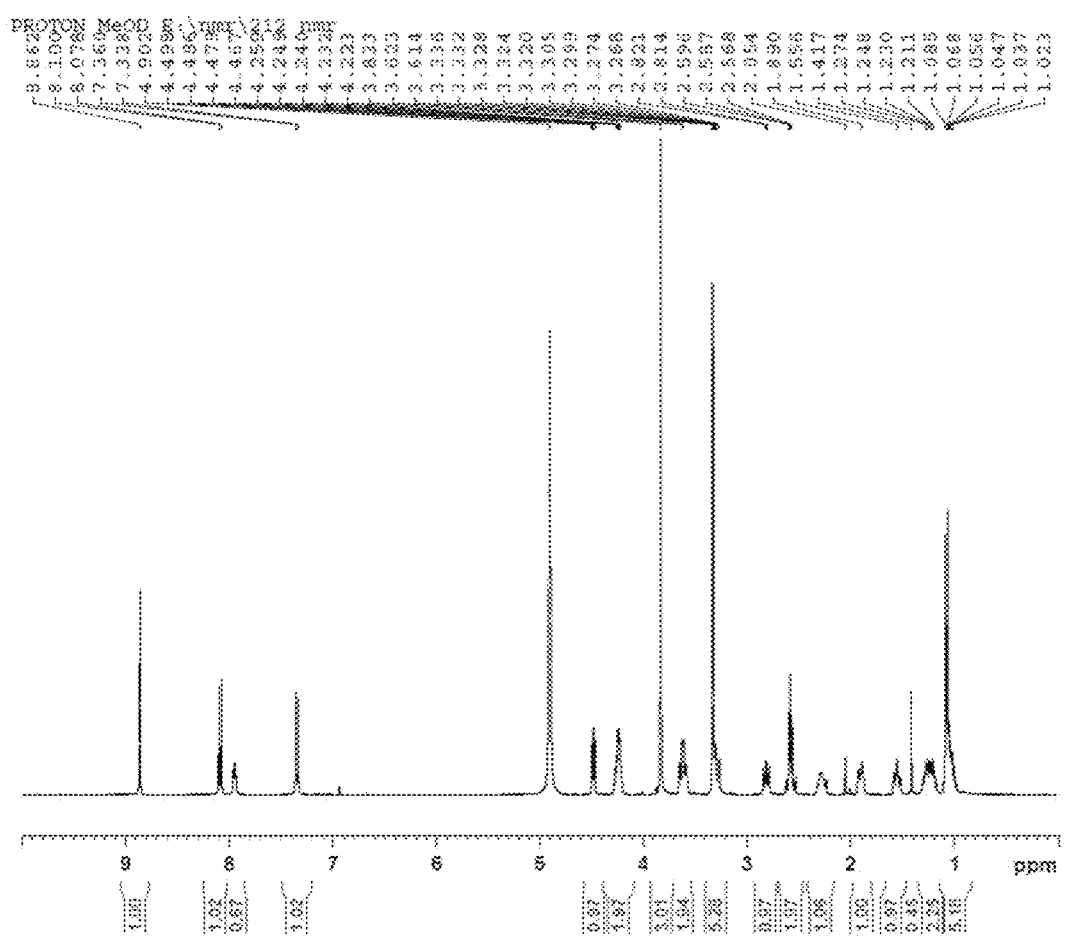
FIG. 5 is a nuclear magnetic resonance hydrogen spectrum of the impurity B.
Figure 6:
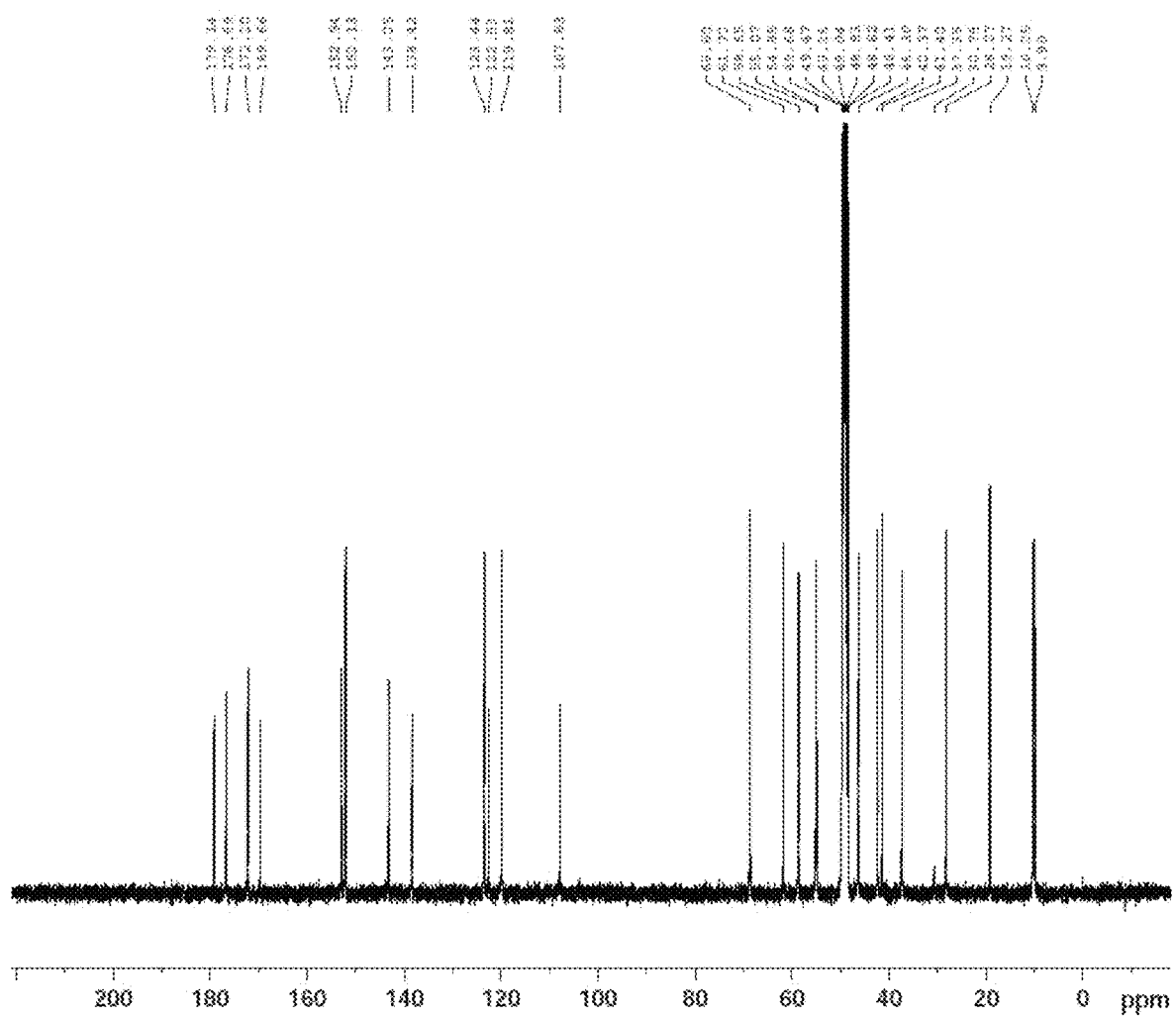
FIG. 6 is a nuclear magnetic resonance carbon spectrum of the impurity B.
Figure 7:
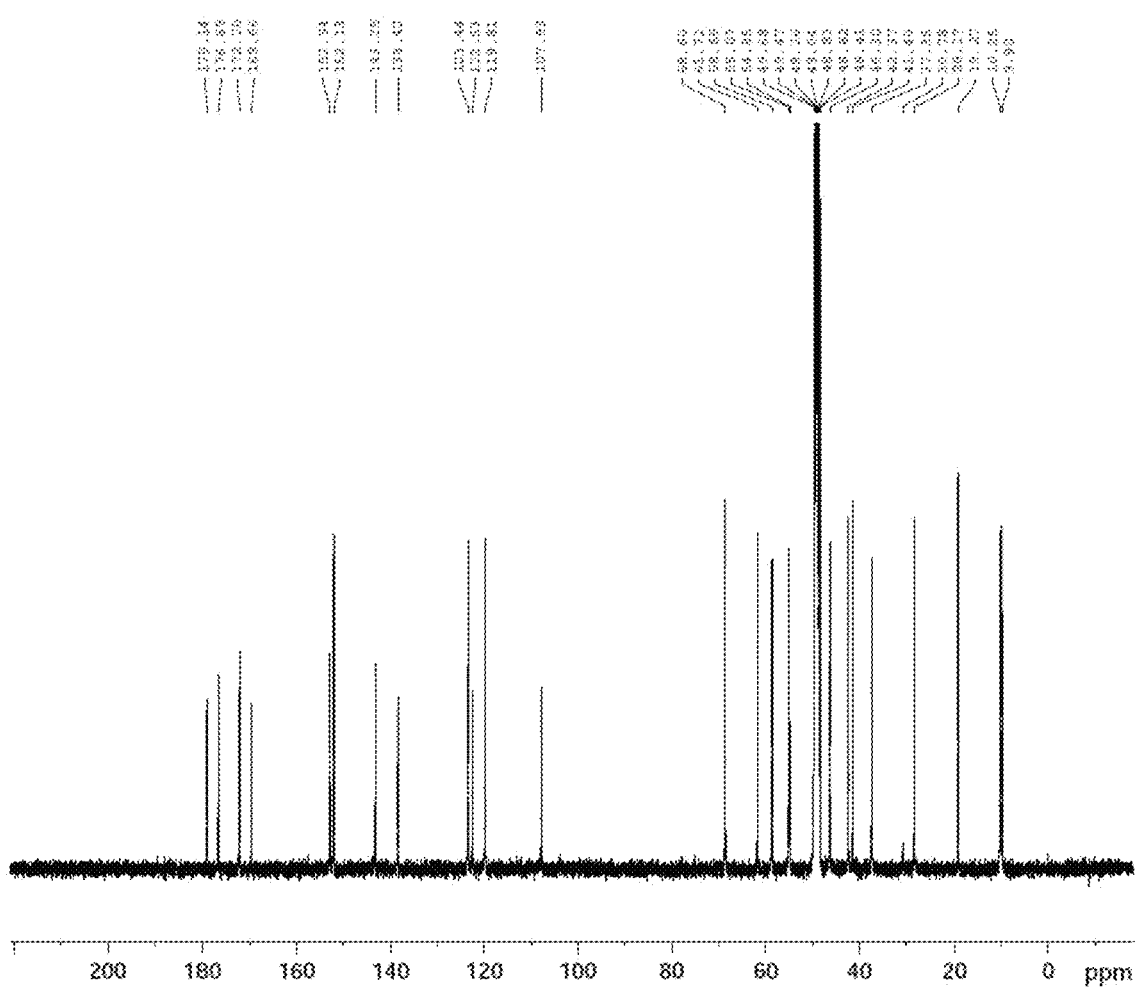
FIG. 7 is a nuclear magnetic resonance hydrogen spectrum of the impurity C.
Figure 8:
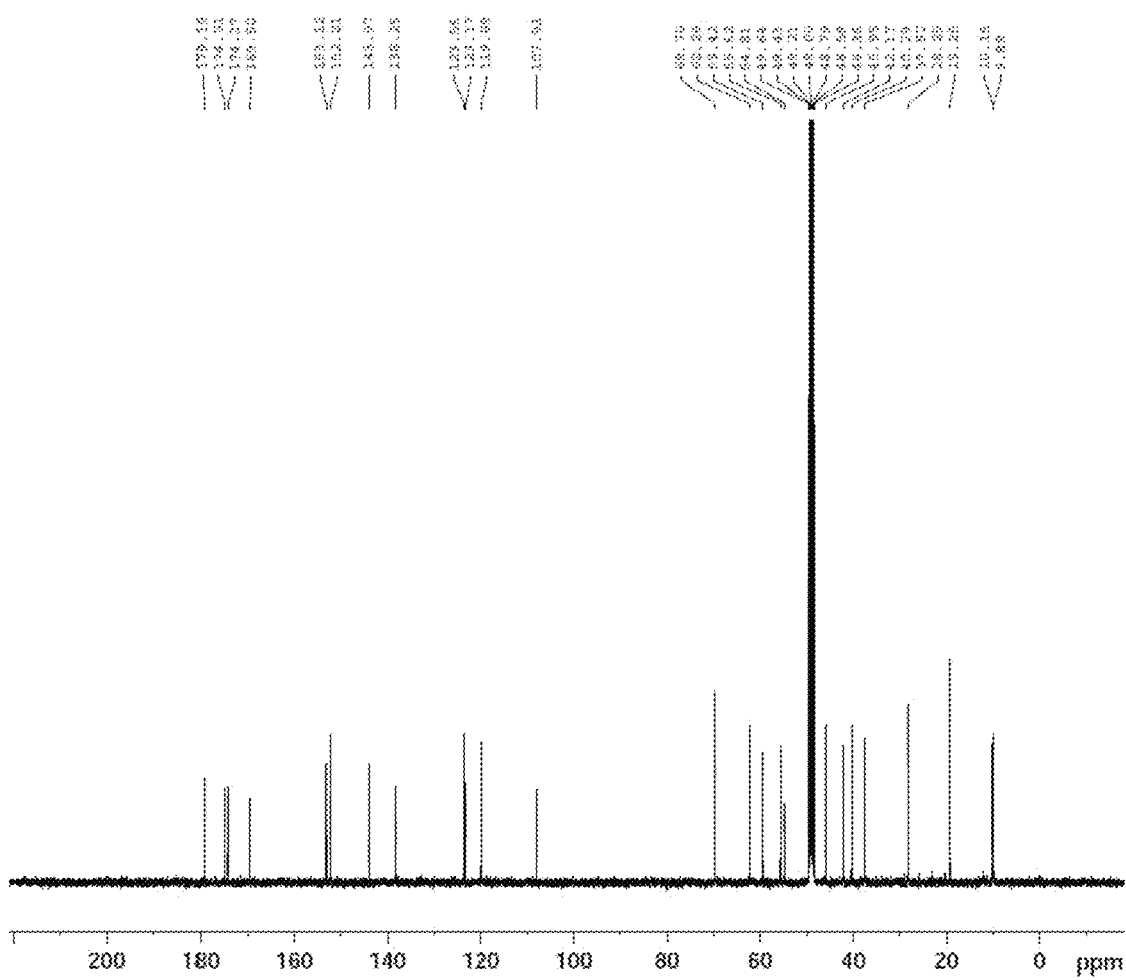
FIG. 8 is a nuclear magnetic resonance carbon spectrum of the impurity C.
Figure 9:
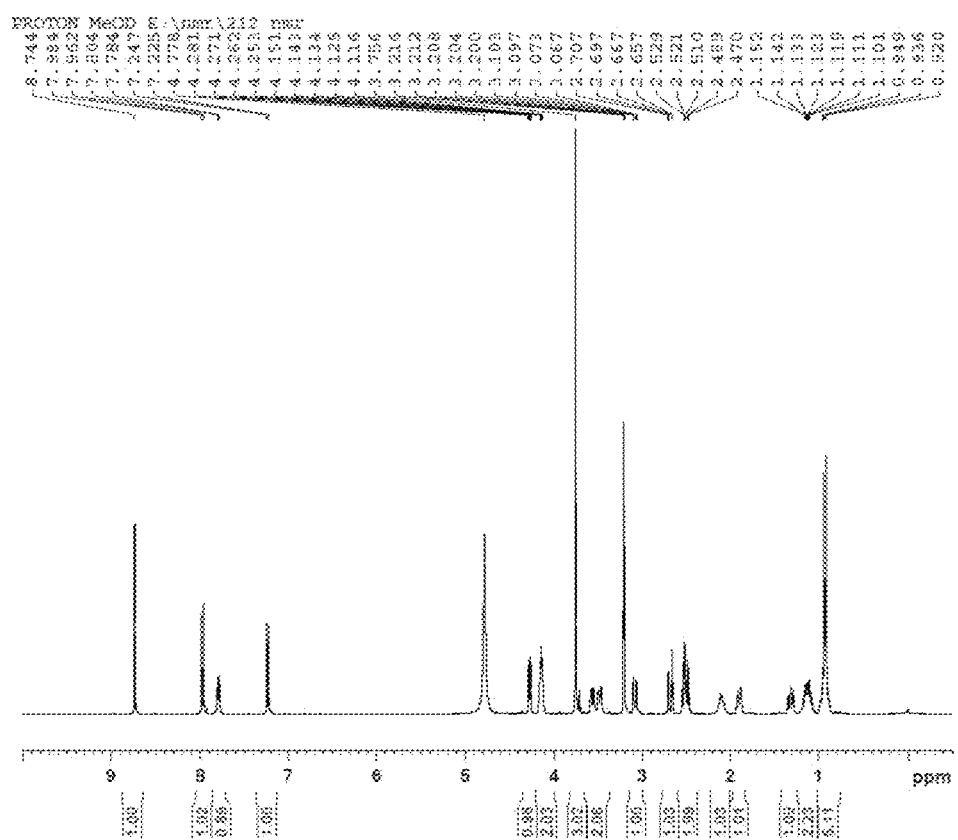
FIG. 9 is a nuclear magnetic resonance hydrogen spectrum of the impurity D.
Figure 10:
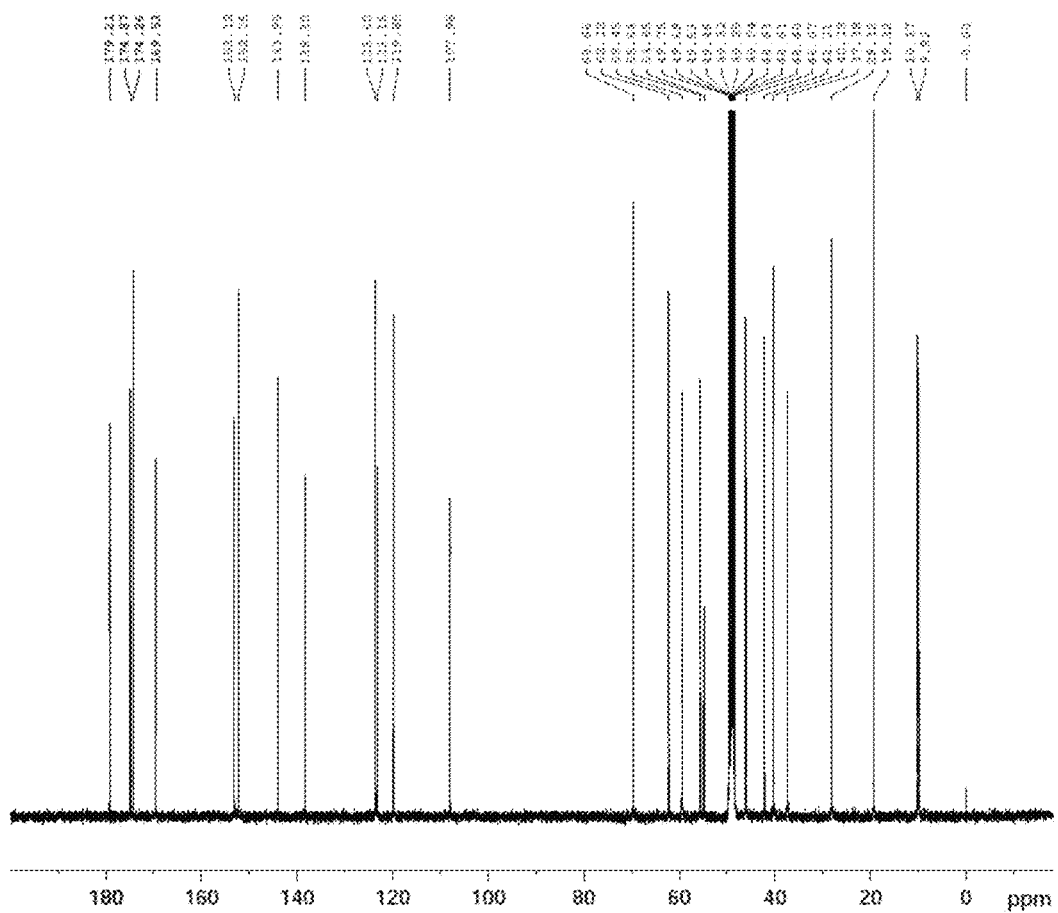
FIG. 10 is a nuclear magnetic resonance carbon spectrum of the impurity D.
Figure 11:
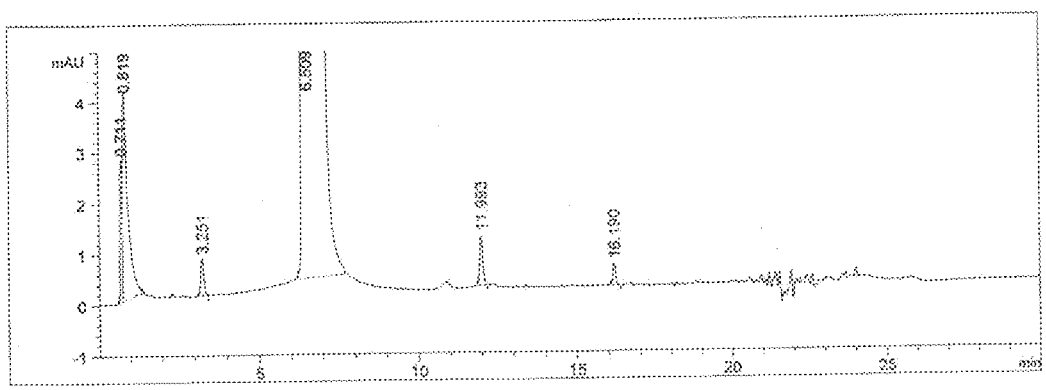
FIG. 11 is an HPLC diagram of the nemonoxacin malate prepared in embodiment 1.

After a long and intensive study, the inventor designed a method for preparing the nemonoxacin malate API, according to the method, the required nemonoxacin malate API may be obtained with extremely high purity (the total content of impurities is lower than 0.15%), thereby effectively avoiding the production of the impurities, in addition, the method is suitable for industrial production as it does not require tedious operations. On the basis of the above findings, the inventor has completed the present disclosure.

Nemonoxacin Malate API

The present disclosure provides a nemonoxacin malate API, in related substances of the API, the sum of four composition impurities A, B, C and D obtained by means of a condensation reaction of D,L-malic acid and nemonoxacin is not greater than 0.15%;

wherein, impurity A:

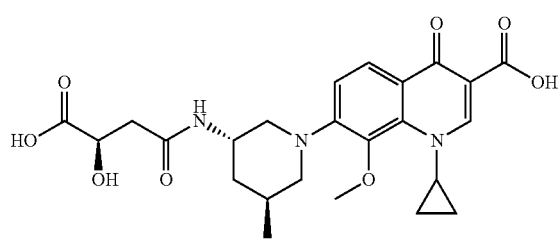 [SMILES: COc1c(N2C[C@@H](C)C[C@H](NC(=O)C[C@@H](O)C(=O)O)C2)ccc2c(=O)c(C(=O)O)cn(C3CC3)c12]

impurity B:

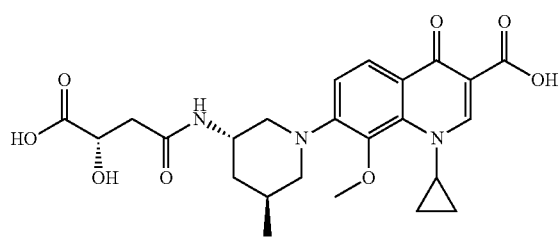 [SMILES: COc1c(N2C[C@@H](C)C[C@H](NC(=O)C[C@H](O)C(=O)O)C2)ccc2c(=O)c(C(=O)O)cn(C3CC3)c12]

impurity C:

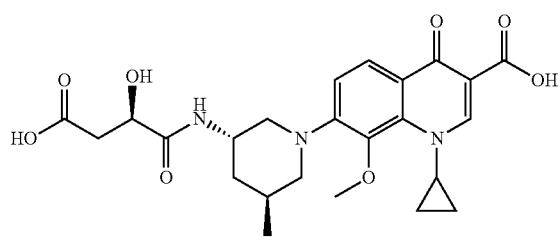 [SMILES: COc1c(N2C[C@@H](C)C[C@H](NC(=O)[C@H](O)CC(=O)O)C2)ccc2c(=O)c(C(=O)O)cn(C3CC3)c12]

impurity D:

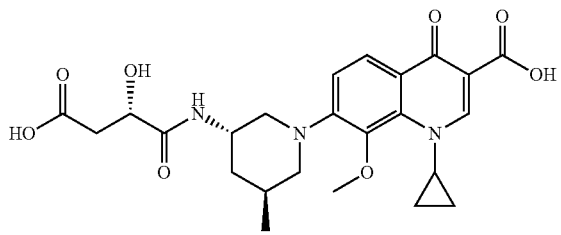 [SMILES: COc1c(N2C[C@@H](C)C[C@H](NC(=O)[C@@H](O)CC(=O)O)C2)ccc2c(=O)c(C(=O)O)cn(C3CC3)c12]

In the present disclosure, the structures of the impurities in the API are clearly characterized, and the content of the impurities is controlled within a qualified range. Quality control indicators are essential to ensure the effectiveness and safety of products, the impurities in the nemonoxacin malate or any API are redundant, and the limit of the impurities can be established in a targeted manner according to the nature of impurities only by clearly defining the impurities, studying the impurities exceeding an identification limit and identifying chemical structures of the impurities, such that the safety and effectiveness of the API and a final preparation can be guaranteed.

Method for Preparing Nemonoxacin Malate API

The present disclosure further provides a method for preparing the nemonoxacin malate API, the method includes the following steps:

1) nemonoxacin free base (Formula II) and D,L-malic acid are dissolved in a 50° C.-65° C. C1-C3 alcohol/water mixed solution, or all materials are mixed and then heated to 50° C.-65° C., the use amount of the mixed solvent is 8-14 times the weight of the nemonoxacin free base, and a weight ratio of water to C1-C3 alcohol is 0.4-0.7:1;

2) cooling crystallization is performed on a mixed solution obtained in the step 1), and then solid-liquid separation, washing and drying are performed on a precipitated solid, so as to obtain the nemonoxacin malate API.

A salifying reaction (that is the step 1) is performed in the mixed solution of C1-C3 alcohol and water, the C1-C3 alcohol may be methanol, ethanol, propanol or isopropanol, preferably the ethanol. In a preferred embodiment of the present disclosure, the weight ratio of the water and the C1-C3 alcohol is 0.4-0.7:1, preferably 0.5-0.6:1.

In the step 1), a dissolving temperature of the nemonoxacin free base and the D,L-malic acid is 50° C.-65° C., preferably 55° C.-60° C. If the temperature is too high, the content of impurities in a product is significantly increased, if the temperature is too low, the salified product is rapidly precipitated, which may include incompletely dissolved nemonoxacin free base and be not conductive to the control of a physical form of the API.

In a preferred embodiment of the present disclosure, a feeding mole ratio of the D,L-malic acid to the nemonoxacin free base is 0.95:1.05-1.2:1.0, preferably 0.98:1.03-1.05:1.0, and optimally, 1.00:1.02-1.0, When the feeding amount of the D,L-malic acid is relatively low, the salifying reaction is incomplete, such that free base residues, resulting in unqualified products, and when the feeding amount is relatively high, the content of the produced impurities is relatively high.

In a preferred embodiment of the present disclosure, in the C1-C3 alcohol/water mixed solution, the use amount of the mixed solvent is 8-14 times the weight of the nemonoxacin free base, preferably 10-12 times, if the feeding amount is not appropriate, crystallization yield and the final physical forms of the products are easily changed.

In the step 1), cooling crystallization may be directly performed on the obtained solution, or may be performed after the solution is decolorized with activated carbon. Preferably, the mixed solution obtained in the step 1) is decolorized with the activated carbon at 50° C.-65° C., and filtrate is obtained after hot filtration; or the solution obtained in the step 1) is filtered and decolorized on line by means of an activated carbon filter. The activated carbon of which weight is 1%-20% of the weight of the nemonoxacin free base is used for decolorization, and the used activated carbon is not specifically limited, the time for the decolorization is 1-60 min, preferably 10-30 min; the activated carbon after hot filtration may be selected to be washed or to not be washed.

In the step 2), the manner of performing cooling crystallization on the solution obtained in the step 1) may select direct cooling crystallization or gradient cooling crystallization, preferably the gradient cooling the crystallization. The manner of the gradient cooling includes: cooling the filtrate to 35° C.-45° C., holding the temperature, and performing stirring for 0.5-6 h, preferably 1-4.5 h, and more preferably 1-3 h; after temperature holding is completed, performing cooling again to −10° C.-20° C., preferably −10° C.-10° C., and more preferably −5° C.-5° C. Filtering is performed; a filter cake is washed with ethanol, and then vacuum drying is performed on the filter cake at 20° C.-65° C., preferably 30-60° C., and more preferably 40-50° C., so as to obtain the nemonoxacin malate API.

In related substances of the nemonoxacin malate API prepared according to the method, the sum of four composition impurities A, B, C and D obtained by means of a condensation reaction of the malic acid and the nemonoxacin is not greater than 0.15%.

Any possible variation or replacement of the present disclosure all fall within the scope of protection of the present disclosure, without departing from the conception of the present disclosure.

Unless otherwise specified, the relevant substance items in the detection method of the present disclosure are performed according to the following method:

an HPLC normalization method: Chromatographic column Agilent C8 column (4.6 mm*150 mm, 5 μm); mobile phase A: 0.1% formic acid aqueous solution, B: 0.1% formic acid acetonitrile solution, gradient elution (0-20 min, A 88%-20%); detection wavelength: 292 nm; column temperature: 40° C.; and flow rate: 1.5 mL/min.

According to the detection method, in the related substances of the nemonoxacin malate API provided in the present disclosure, the sum of the four composition impurities A, B, C and D obtained by means of a condensation reaction of the malic acid and the nemonoxacin is not greater than 0.15%. The relative retention time (using the retention time of the nemonoxacin being about 6.5 min as reference) of the impurities A, B, C and D is all about 2.5.

Compared with the prior art, the main advantages of the present disclosure include the following:

1) the nemonoxacin malate API provided in the present disclosure is high in purity, the composition impurities are low in level, and the quality control indicators can guarantee the safety and effectiveness of the products.
2) by means of the process of the present disclosure, the D,L-malic acid and the nemonoxacin free base may be salified at a relatively low temperature, thereby greatly reducing the production of the composition impurities.
3) by means of the process of the present disclosure, the water consumption during salifying is increased, dissolution time of a salifying solution is obviously shortened, the composition impurities are reduced, and the optimization of the ratio of a salifying solvent causes a crystallization process to be more stable.
4) by means of the process of the present disclosure, the yield of finished products is obviously increased, so as to achieve greater economic advantages.

The present disclosure is further described below with reference to the specific embodiments. It should be understood that, these embodiments are only intended to describe the present disclosure and are not intended to limit the scope of the present disclosure. Experimental methods for which specific conditions are not indicated in the following embodiments usually follow conventional conditions, or follow the conditions recommended by manufacturers. Percentages and parts are calculated by weight unless otherwise specified.

The nemonoxacin free base (Formula II) may be prepared by means of any method in the prior art, for example, a method shown in CN 101045725 B. The composition impurities A, B, C and D may be prepared by means of any method in the prior art, for example, a salifying mother solution obtained by means of the method shown in CN 101045725 B is obtained by means of preparing a liquid phase and performing separation and purification. Unless otherwise specified, the relevant substance items in the detection method of the present disclosure are performed according to the method described in the content of the present disclosure.

Embodiment 1

145 g of anhydrous ethanol and 80 g of water were added to a 500 mL three-necked bottle, and a temperature was risen to 60° C. under stirring. 20.5 g (containing 6% of water, 51.9 mmol) of the nemonoxacin free base (Formula II) and 7.0 g (52.2 mmol) of the D,L-malic acid were added to the three-necked bottle, and a reaction solution was clear. 1 g of the activated carbon was added to the solution, stirring was performed for 10 min in a manner of temperature holding, and then hot filtration was performed. The filtrate was cooled to 40° C. and stirred for about 2 h in a manner of temperature holding, and then a crystallization solution was further cooled to 0° C. Filtration was performed, the filter cake was washed with the anhydrous ethanol, and a wet product was dried for 12 h at 45° C., so as to obtain 21.9 g of the nemonoxacin malate (molar yield being 82.0%).

HPLC analysis was performed on the product, by area normalization, the purity of the nemonoxacin malate was 99.50%, and the sum of the impurities A, B, C and D was 0.02% (peaks appear at the same retention time, about 16.1 min). Nuclear magnetic analysis was performed on the nemonoxacin malate obtained by means of separation and the impurities A, B, C and D, and results were shown as follows:

1. Determination of the Structure of the Nemonoxacin Malate $^1$H NMR (400 MHz, DMSO-$d_6$) δ:8.71 (s, 1H), 8.03 (d, J=8.8 Hz, 1H), 7.36 (d, J=8.8 Hz, 1H), 4.18-4.22 (m, 1H), 3.89 (dd, J=4.0, 10.0 Hz, 1H), 3.74 (s, 3H), 3.62 (s, 1H), 3.35-3.46 (m, 4H), 2.86 (dd, J=8.0, 12.0 Hz, 1H), 2.52 (q, J=10.0 Hz, 1H), 2.31 (dd, J=4.0, 15.6 Hz, 1H), 2.25-2.28 (m, 1H), 1.82-1.86 (m, 1H), 1.62-1.66 (m, 1H), 1.11-1.19 (m, 2H), 1.02 (d, J=6.4 Hz, 3H), 0.98-1.06 (m, 2H). MS: [M+H]$^+$ 372.2.

2. Determination of the Structures of the Four Composition Impurities

Impurity A:
$^1$H NMR (400 MHz, CD$_3$OD) δ:8.85 (s, 1H), 8.06 (d, J=8.8 Hz, 1H), 7.99 (d, J=7.2 Hz, CONH), 7.33 (d, J=8.8 Hz, 1H), 4.45 (dd, J=4.0, 7.8 Hz, 1H), 4.22-4.28 (ovlapped, 2H), 3.84 (s, 3H), 3.66 (dd, J=3.2, 12.0 Hz, 1H), 3.60 (dd, J=4.0, 12.0 Hz, 1H), 3.27 (dd, J=2.4, 12.2 Hz, 1H), 2.77 (dd, J=9.2, 12.0 Hz, 1H), 2.71 (dd, J=4.4, 15.2 Hz, 1H), 2.56 (dd, J=8.0, 15.2 Hz, 1H), 2.27-2.29 (m, 1H), 1.86-1.91 (m, 1H), 1.51-1.57 (m, 1H), 1.19-1.30 (m, 2H), 1.01-1.08 (m, 5H). MS: [M+H]$^+$488.2.

Impurity B:
$^1$H NMR (400 MHz, CD$_3$OD) δ:8.86 (s, 1H), 8.09 (d, J=8.8 Hz, 1H), 7.95 (d, J=7.0 Hz, CONH), 7.35 (d, J=8.8 Hz, 1H), 4.48 (dd, J=4.8, 7.6 Hz, 1H), 4.22-4.27 (ovlapped, 2H), 3.83 (s, 3H), 3.58-3.65 (ovlapped, 2H), 3.29 (dd, J=2.4, 12.4 Hz, 1H), 2.82 (dd, J=8.8, 11.8 Hz, 1H), 2.57-2.60 (ovlapped, 2H), 2.28-2.29 (m, 1H), 1.88-1.92 (m, 1H), 1.52-1.59 (m, 1H), 1.19-1.30 (m, 2H), 1.00-1.09 (m, 5H). MS: [M+H]$^+$ 488.2.

Impurity C:
$^1$H NMR (400 MHz, CD$_3$OD) δ:8.86 (s, 1H), 8.07 (d, J=8.8 Hz, 1H), 7.35 (d, J=8.8 Hz, 1H), 4.44 (dd, J=3.6, 8.4 Hz, 1H), 4.23-4.26 (ovlapped, 2H), 3.88 (s, 3H), 3.68 (d, J=8.8 Hz, 1H), 3.57 (d, J=10.4 Hz, 1H), 3.21 (dd, J=2.0, 12.0 Hz, 1H), 2.78 (dd, J=3.6, 16.2 Hz, 1H), 2.65 (t, J=10.8 Hz, 1H), 2.50 (dd, J=8.4, 16.2 Hz, 1H), 2.16-2.21 (m, 1H), 1.98-2.01 (m, 1H), 1.42-1.49 (m, 1H), 1.18-1.30 (m, 2H), 1.01-1.11 (m, 5H).
MS: [M+H]$^+$1488.2.

Impurity D:
$^1$H NMR (400 MHz, CD$_3$OD) δ:8.74 (s, 1H), 7.97 (d, J=8.4 Hz, 1H), 7.79 (d, J=8.0 Hz, CONH), 7.24 (d, J=8.4 Hz, 1H), 4.27 (dd, J=4.0, 7.6 Hz, 1H), 4.11-4.15 (ovlapped, 2H), 3.76 (s, 3H), 3.56 (dd, J=2.8, 10.8 Hz, 1H), 3.48 (d, J=10.8 Hz, 1H), 3.09 (dd, J=2.4, 12.0 Hz, 1H), 2.68 (dd, J=4.0, 16.0 Hz, 1H), 2.52 (t, J=10.8 Hz, 1H), 2.50 (dd, J=7.6, 16.0 Hz, 1H), 2.09-2.12 (m, 1H), 1.88-1.92 (m, 1H), 1.28-1.35 (m, 1H), 1.08-1.18 (m, 2H), 10.88-0.98 (m, 5H). MS: [M+H]$^+$ 488.2.

Embodiment 2

120 g of the anhydrous ethanol, 60 g of the water, 20.5 g (containing 6% of water, 51.9 mmol) of the nemonoxacin free base (Formula II) and 7.4 g (55.5 mmol) of the D,L-malic acid were added to the 500 mL three-necked bottle, the temperature was risen to 63° C. under stirring, and the reaction solution was clear. 1.5 g of the activated carbon was added to the solution, stirring was performed for 20 min in a manner of temperature holding, and then hot filtration was performed. The filter cake was washed with the ethanol (10 g) which was preheated to 60° C.; the filtrate and the washing solution were merged, cooled to 40° C., and stirred for about 2 h in a manner of temperature holding; and then a crystallization solution was further cooled to 0° C. Filtration was performed, the filter cake was washed with the anhydrous ethanol, and a wet product was dried for 15 h at 40° C., so as to obtain 22.2 g of the nemonoxacin malate (molar yield being 83.0%).

By area normalization, the purity of the nemonoxacin malate was 99.90%, and the sum of the impurities A, B, C and D was 0.04% (peaks appear at the same retention time, about 16.1 min).

Embodiment 3

390 g of anhydrous ethanol and 260 g of water were added to a 1000 mL three-necked bottle, and a temperature was risen to 50° C. under stirring. 50 g (containing 6% of water, 126.5 mmol) of the nemonoxacin free base (Formula II) and 16.4 g (122.7 mmol) of the D,L-malic acid were added to the three-necked bottle, and stirring was performed until the reaction solution was clear. The solution was naturally cooled to room temperature, and then was cooled to 5° C. by means of an ice bath. Filtration was performed, the filter cake was washed with the anhydrous ethanol, and a wet product was dried for 15 h at 45° C., so as to obtain 50.8 g of the nemonoxacin malate (molar yield being 78.0%).

By area normalization, the purity of the nemonoxacin malate was 100.00%, and the impurities A, B, C and D were not detected.

Embodiment 4

390 g of anhydrous ethanol and 260 g of water were added to a 1000 mL three-necked bottle, and a temperature was risen to 50° C. under stirring. 50 g (containing 6% of water, 126.5 mmol) of the nemonoxacin free base (Formula II) and 20.4 g (151.8 mmol) of the D,L-malic acid were added to the three-necked bottle, and stirring was performed in a manner of temperature holding. The solution was naturally cooled to room temperature, and was then cooled to -5° C. by means of an ice bath. Filtration was performed, the filter cake was washed with the anhydrous ethanol, and a wet product was dried for 10 h at 55° C., so as to obtain 52.1 g of the nemonoxacin malate (molar yield being 80.0%).

By area normalization, the purity of the nemonoxacin malate was 99.92%, and the sum of the impurities A, B, C and D was 0.08%.

Figure 12:
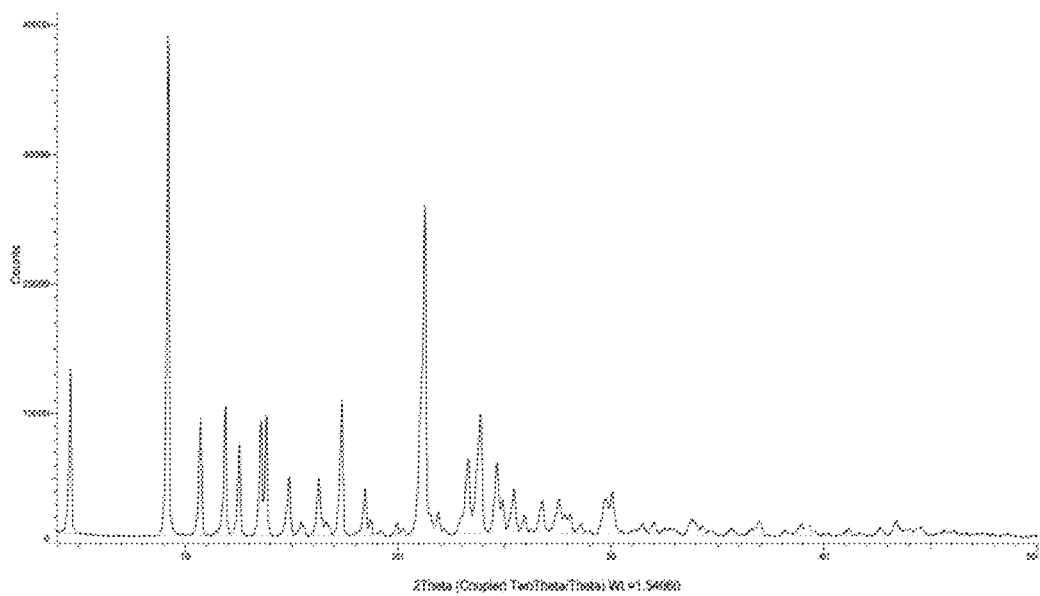
FIG. 12 is an XPRD diagram of the nemonoxacin malate prepared in embodiment 1.
Figure 13:
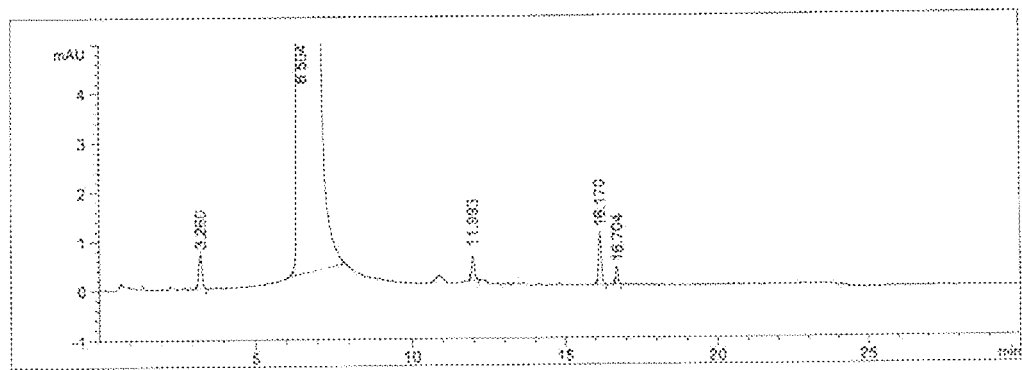
FIG. 13 is an HPLC diagram of the nemonoxacin malate prepared in embodiment 2.
Figure 14:
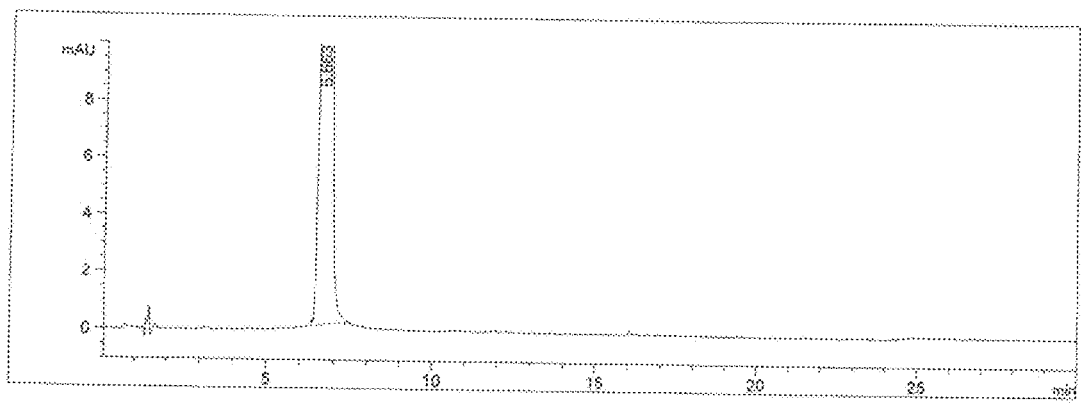
FIG. 14 is an HPLC diagram of the nemonoxacin malate prepared in embodiment 3.
Figure 15:
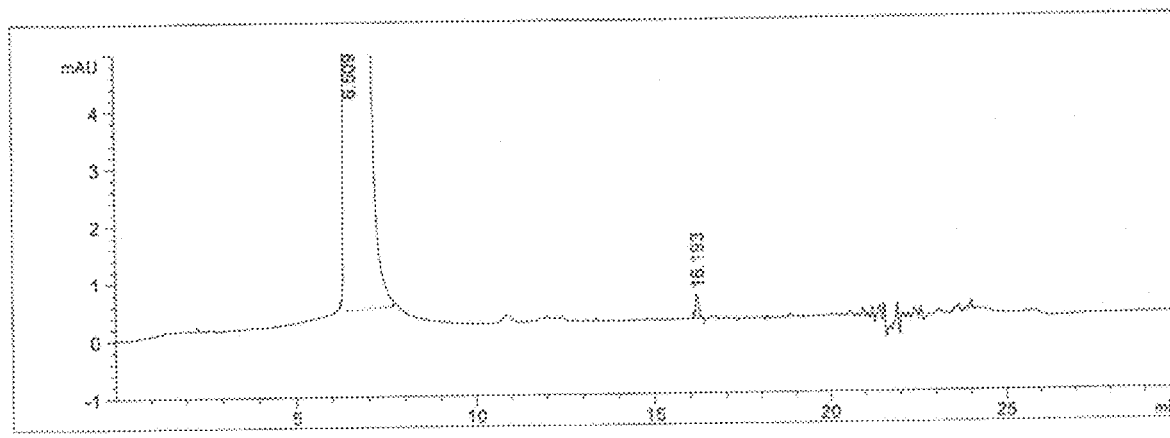
FIG. 15 is an HPLC diagram of the nemonoxacin malate prepared in embodiment 4.
Figure 16:
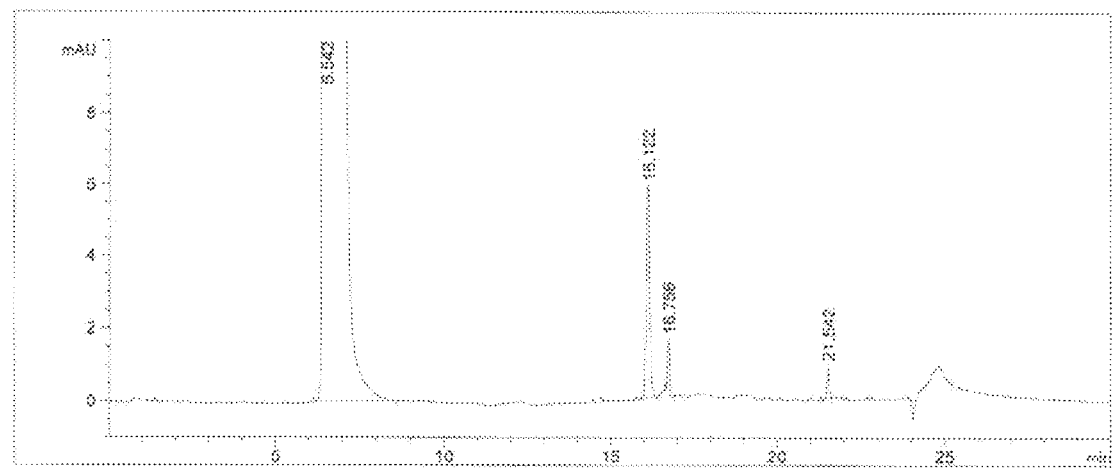
FIG. 16 is an HPLC diagram of the nemonoxacin malate prepared in comparative example 1.
Figure 17:
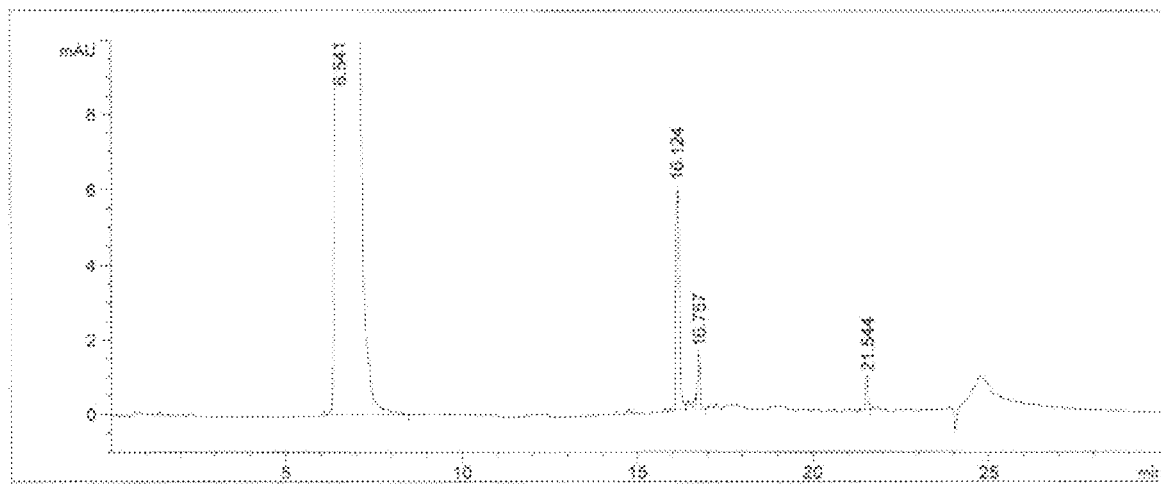
FIG. 17 is an HPLC diagram of the nemonoxacin malate prepared in comparative example 2.
Figure 18:
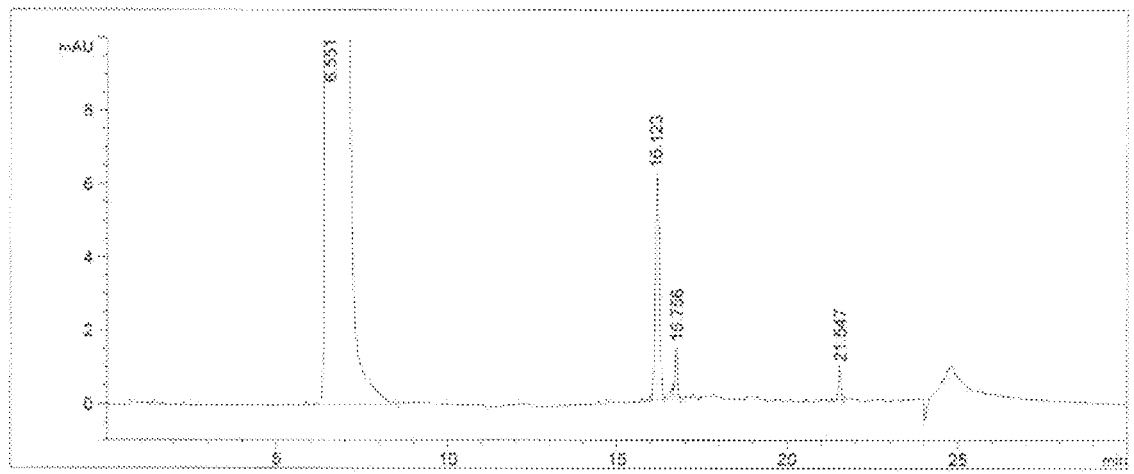
FIG. 18 is an HPLC diagram of the nemonoxacin malate prepared in comparative example 4.

The crystal form of the nemonoxacin malate obtained in the above embodiments was consistent with the stable crystal form of the D,L-malate hemihydrate described in the Patent CN101045725B, referring to FIG. 12.

Comparative Example 1 (Preparation of Nemonoxacin Malate Using Nemonoxacin Free Base (Formula II) by Means of the Method in CN 101045725 B)

32 g (containing 6% of water, 80.96 mmol) of nemonoxacin free base (Formula II) was put into a reaction flask, and the solid was suspended in 256 g of 95% ethanol acting as a solvent. Then 11 g of a solid D,L-malic acid was added to the reaction, and the mixture was heated to a reflux temperature (about 80° C.). Distilled water (about 57 mL) was added to the reaction flask until the mixture was completely dissolved, and 2 g of activated carbon was added. Filtration was performed, cooling was performed to 45° C., and storage was performed for at least 2 hours for crystallization. The reaction mixture was further cooled to 5° C., and a suspended solid was separated by means of suction filtration, then 66 g of the 95% ethanol was used to wash the solid, and vacuum drying was performed for at least 4 hours. Then the solid was further dried for at least 12 hours at 45° C. in a convection oven, so as to obtain 29.2 g of the nemonoxacin malate API (molar yield being about 70%).

By area normalization, the purity of the nemonoxacin malate was 99.75%, and the sum of the impurities A, B, C and D was 0.18%.

It may be learned from results that, compared with the API provided in the present disclosure, in the nemonoxacin malate API obtained in the comparative embodiment, the content of the composition impurities was relatively high, such that it was difficult to guarantee the safety and effectiveness of subsequent preparation administration. In addition, a salifying process provided in the present disclosure was stable, controllable and high in yield, such that the present disclosure has greater economic advantages.

Comparative Example 2 (Recrystallization)

160 g of the ethanol (95%), 20 g of nemonoxacin malate (Formula I) and 36 mL of water were added to the 500 mL three-necked bottle, heated to 82° C., and stirred in a manner of temperature holding, and the reaction solution was clear. Cooling was performed to 40° C., stirring was performed for about 2 h, and then a crystallization solution was further cooled to 5° C. Filtration was performed, the filter cake was washed with the 95% ethanol, and a wet product was dried for 12 h at 45° C., so as to obtain 16.4 g of the nemonoxacin malate (molar yield being 82.0%).

By area normalization, the purity of the nemonoxacin malate was 99.66%, and the sum of the impurities A, B, C and D was 0.27%.

It may be learned from results that, the content of the composition impurities in the nemonoxacin malate API after recrystallization was increased, such that it was difficult to guarantee the safety and effectiveness of subsequent preparation administration, therefore, recrystallization was not taken into consideration in the final preparation method.

Comparative Example 3 (Reducing a Crystallization Temperature According to Comparative Example 1)

160 g of the ethanol (95%), 20 g (containing 6% of water, 50.6 mmol) of the nemonoxacin free base (Formula II), 6.9 g of the solid D,L-malic acid and 36 mL of the water were added to the 500 mL three-necked bottle, heated to 55° C. and stirred in a manner of temperature holding; and then 1.3 g of the activated carbon was added, and there was no dissolving process. Hot filtration was performed, the filtrate was cooled to 45° C. and stirred for about 2 h in a manner of temperature holding, and then the crystallization solution was further cooled to 5° C. Filtration was performed, the filter cake was washed with the 95% ethanol, and a wet product was dried for 12 h at 45° C., so as to obtain 18.1 g of the nemonoxacin malate (molar yield being 65.3%).

In this comparative embodiment, there was no dissolving process in the salifying process, the free base cannot be completely salified by being wrapped in the malate, affecting the quality of products. In addition, decolorization and filtration were performed with the activated carbon, part of the products was also filtered, resulting in relatively large yield loss, such that this comparative embodiment was difficult to be used in industrial production.

Comparative Example 4 (Repeating Operations in Embodiment 1, High Temperature Salifying)

141 g of the ethanol, 20 g (containing 6% of water, 50.6 mmol) of the nemonoxacin free base (Formula II), 6.9 g of the solid D,L-malic acid and 78 mL of the water were added to the 500 mL three-necked bottle, heated to 80° C. and stirred; and then 1 g of the activated carbon was added, and the reaction solution was clear. Hot filtration was performed. The filtrate was cooled to 40° C. and stirred for about 2 h in a manner of temperature holding, and then a crystallization solution was further cooled to 0° C. Filtration was performed, the filter cake was washed with the anhydrous ethanol, and a wet product was dried for 12 h at 45° C., so as to obtain 53.9 g of the nemonoxacin malate (molar yield being 82.8%).

By area normalization, the purity of the nemonoxacin malate was 99.73%, and the sum of the impurities A, B, C and D was 0.20%. Results show that, if temperature conditions change, the content of the impurities exceeds an allowable limit, suggesting that temperature control in the preparation method greatly affects the preparation effect.

All literature mentioned in the present disclosure is cited by reference in this application as if each piece of the literature were cited separately as a reference. In addition, it should be understood that, after reading the above lecturing content in the present disclosure, a person skilled in the art may make various alterations or modifications to the present disclosure, and these equivalent forms likewise fall within the scope defined by the claims appended to this application.

What is claimed is:

1. A method for preparing a nemonoxacin malate API, comprising the following steps:
   1) Providing a C1-C3 alcohol/water mixed solvent in which nemonoxacin free base and D,L-malic acid are dissolved, the temperature of the mixed solvent is 50° C.-65° C.,
      wherein, a feeding mole ratio of the D,L-malic acid to the nemonoxacin free base is 0.95:1.0-1.2:1.0, the use amount of the C1-C3 alcohol/water mixed solvent is 8-14 times the weight of the nemonoxacin free base, and a weight ratio of the water to the C1-C3 alcohol is 0.4-0.7:1;
   2) Performing cooling crystallization on a mixed solution obtained in the step 1), and then performing solid-liquid separation, washing and drying on a precipitated solid, so as to obtain the nemonoxacin malate API;
   the cooling crystallization refers to direct cooling crystallization; and the direct cooling crystallization comprises: cooling the mixed solution to room temperature, and then performing cooling to −10° C.-20° C. by means of an ice bath for crystallization; or
   the cooling crystallization refers to gradient cooling crystallization, the gradient cooling crystallization comprises the following steps:
   (i) cooling the mixed solution to 35° C.-45° C., then holding the temperature and performing stirring for 0.5-6 h;
   (ii) cooling filtrate obtained in the step (i) to −10° C.-20° C. for crystallization;
   (iii) filtering the filtrate after the crystallization, washing a filter cake with ethanol, and then performing vacuum drying on the filter cake at 20° C.-65° C. so as to obtain the nemonoxacin malate API.

2. The method for preparing the nemonoxacin malate API according to claim 1, wherein the temperature of the mixed solvent is 55° C.-60° C.

3. The method for preparing the nemonoxacin malate API according to claim 1, wherein the use amount of the C1-C3 alcohol/water mixed solvent is 10-12 times the weight of the nemonoxacin free base.

4. The method for preparing the nemonoxacin malate API according to claim 1, wherein a weight ratio of water to C1-C3 alcohol is 0.5-0.6:1.

5. The method for preparing the nemonoxacin malate API according to claim 1, wherein the feeding mole ratio of the D,L-malic acid to the nemonoxacin free base is 0.98:1.03-1.05:1.0.

6. The method for preparing the nemonoxacin malate API according to claim 1, wherein before cooling crystallization, the method further comprises the following step: using activated carbon to decolorize the mixed solution.

7. The method for preparing the nemonoxacin malate API according to claim 1, wherein performing cooling to −10° C.-10° C. by means of an ice bath for crystallization.

8. The method for preparing the nemonoxacin malate API according to claim 1, wherein performing cooling to −5° C.-5° C. by means of an ice bath for crystallization.

9. The method for preparing the nemonoxacin malate API according to claim 1, wherein holding the temperature and performing stirring for 1-4.5 h.

10. The method for preparing the nemonoxacin malate API according to claim 1, wherein holding the temperature and performing stirring for 1-3 h.

11. The method for preparing the nemonoxacin malate API according to claim 1, wherein cooling filtrate obtained in the step (i) to −10° C.-10° C. for crystallization.

12. The method for preparing the nemonoxacin malate API according to claim 1, wherein cooling filtrate obtained in the step (i) to −5° C.-5° C. for crystallization.

13. The method for preparing the nemonoxacin malate API according to claim 1, wherein performing vacuum drying on the filter cake at 30-60° C. so as to obtain the nemonoxacin malate API.

14. The method for preparing the nemonoxacin malate API according to claim 1, wherein performing vacuum drying on the filter cake at 40-50° C. so as to obtain the nemonoxacin malate API.

\* \* \* \* \*